US00PP24547P3

(12) United States Plant Patent
Egger

(10) Patent No.: US PP24,547 P3
(45) Date of Patent: Jun. 10, 2014

(54) ***HEUCHERA* PLANT NAMED 'FROST'**

(50) Latin Name: ***Heuchera* hybrid**
Varietal Denomination: Frost

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 140 days.

(21) Appl. No.: 13/507,936

(22) Filed: Aug. 7, 2012

(65) Prior Publication Data

US 2014/0047603 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small almost black leaves with silver veiling over all except reticulate vein pattern, spring leaves of dark purple with almost black veins, light pink flowers on short, dark flower stalks, a small, multi-crowned, low mounding habit, and excellent vigor.

1 Drawing Sheet

Botanical denomination: *Heuchera* hybrid.
Variety designation: 'Frost'.

BACKGROUND OF THE INVENTION

The present invention relates to a new and distinct cultivar of *Heuchera* and given the cultivar name of 'Frost'. *Heuchera* is in the family Saxifragaceae. *Heuchera* 'Frost' originated from a controlled cross between *Heuchera* K329-1, a proprietary non-commercial hybrid, as the seed parent, and *Heuchera* K210-4-1, a proprietary non-commercial hybrid, as the pollen parent.

Compared to the seed parent, *Heuchera* K329-1, the new cultivar has a much smaller leaf and habit.

Compared to the pollen parent, *Heuchera* K210-4-1, the new cultivar has a much smaller leaf and habit and purple to silver leaves rather than rose colored leaves.

Compared to *Heuchera* 'Shanghai', U.S. Plant Pat. No. 21,859, the new cultivar forms a lower mound that does not get "stemmy" over time, has light pink rather than cream colored flowers, and has main veins that are prominently dark rather than all the veins.

Compared to *Heuchera* 'Sugar Berry', U.S. Plant patent application Ser. No. 13/507,974, the new cultivar has smaller leaves, more reticulate dark veins, and leaf margins that are not slightly wavy. The spring leaves of the new cultivar are darker purple and more purple-colored.

This new *Heuchera* is uniquely distinguished by:

1. small almost black leaves with silver veiling over all except reticulate vein pattern,
2. spring leaves dark purple with almost black veins,
3. light pink flowers on short, dark flower stalks,
4. repeat blooming,
5. a small, multi-crowned, low mounding habit, and
6. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 15-month-old plant of *Heuchera* 'Frost' growing in a ½ gallon pot in grown a cold greenhouse in late March in Canby, Oreg.

FIG. 2 shows a nine-month-old plant of *Heuchera* 'Frost' growing in a ½ gallon pot in a cool greenhouse in late September in Canby, Oreg.

DETAILED PLANT DESCRIPTION

The following is a detailed description of the new *Heuchera* cultivar based on observations of 15-month-old specimens growing in ½ gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—17 cm tall from top of the foliage to the soil and 29 cm wide.
*Habit.*—Mounding.
*Vigor.*—Excellent.

Leaf:

*Type.*—Simple.
*Number.*—About 50.

*Arrangement.*—Rosette.
*Shape.*—Broadly ovate to orbicular.
*Size.*—4 mm long and 3 mm wide.
*Lobing/division.*—5 to 7 shallow lobes.
*Venation.*—Palmate.
*Margins.*—Crenate.
*Apex.*—Mucronulate.
*Base.*—Cordate.
*Blade size.*—Grows to 9 cm long and 8.5 cm wide, most leaves are grows to 6.5 cm long and 6 cm wide.
*Texture.*—Supple.
*Surface texture.*—Glandular on top and bottom side.
*Petiole description.*—Grows to 10 cm long and 2 mm wide, glandular hairs, Greyed Purple N187A.
*Leaf color.*—Topside, new leaves in spring between Purple 79B and Purple N77C with veins Black 203A, bottom side Purple N79A; summer to winter leaves between Black 202B and 202C with veins Black 203C, bottom side Purple N79A.

Inflorescence:
*Size.*—Grows to 3.5 cm wide and 9 cm long.
*Type.*—Thyrse.
*Number of flowers per thyrse.*—About 50.
*Number of thyrse.*—About 15 in the first spring flush, reblooming all summer to frost.
*Peduncle.*—Grows to 10 cm long, 1.5 mm wide at base, Purple N77A, glandular hairs.
*Pedicel.*—Variable in size, with glandular hairs, Purple N77A.
*Bloom period.*—May through October in Canby, Oreg.

Flower bud:
*Size.*—2 mm wide and 3 mm long.
*Description.*—Glandular puberulent, ovoid, down facing.
*Color.*—Red Purple 70C on the bottom ⅓ and 69C on the top ⅔.

Flower:
*Type.*—Perfect.
*Shape.*—Campanulate.
*Size.*—4 mm long and 5 mm wide.
*Corolla description.*—5 petals, 3 mm long and 0.4 mm wide, spatulate, usually reflexed, margins entire, tip acute, glabrous top and glandular on bottom, White NN155C.
*Calyx description.*—Campanulate, 4 mm long and 6 mm wide, with 5 lobes divided ⅔ way to the base, each 1.5 mm wide and 2.5 mm long, glandular hairs outside and inside, tips obtuse, margin entire; color inside Red Purple 69C, outside bottom ⅓ Red Purple 70C, top Red Purple 69C with center of lobes tinted 70C.
*Stamen description.*—5 in number, filaments 2 mm long, White NN155C, anthers 0.2 mm, Greyed Orange 179A, pollen none.
*Pistil description.*—1, 2-beaked, 4 mm long and 2 mm wide, White NN155C overall; ovary 1.5 mm long and 2 mm wide, style 2.5 mm long.
*Fragrance.*—None.
*Lastingness.*—Each thyrse blooms for about 3 weeks on the plant.

Fruit:
*Type.*—Two-beaked ovoid capsule.
*Fertility.*—Low.
*Color.*—Greyed Brown 199C.

Seed:
*Shape.*—Linear.
*Size.*—2 mm long.
*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

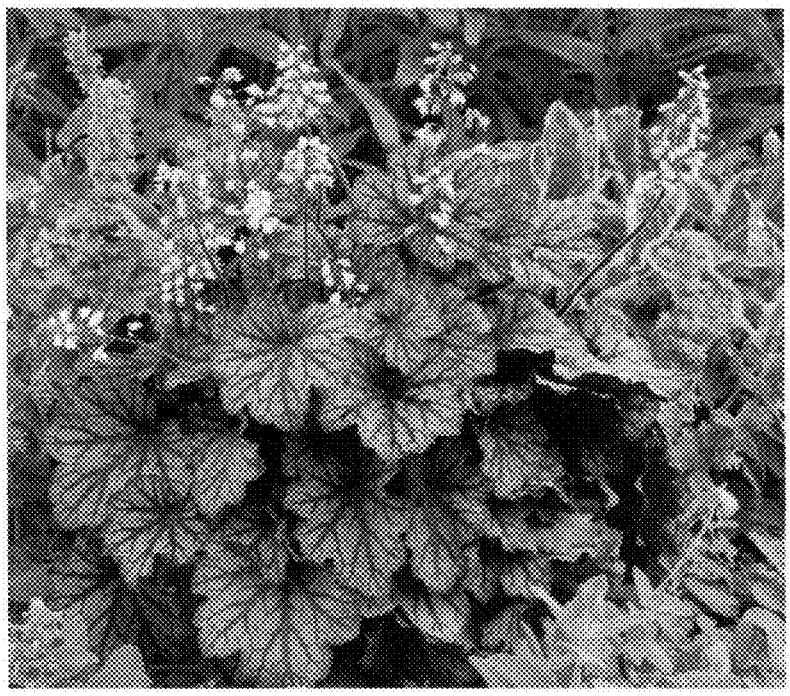

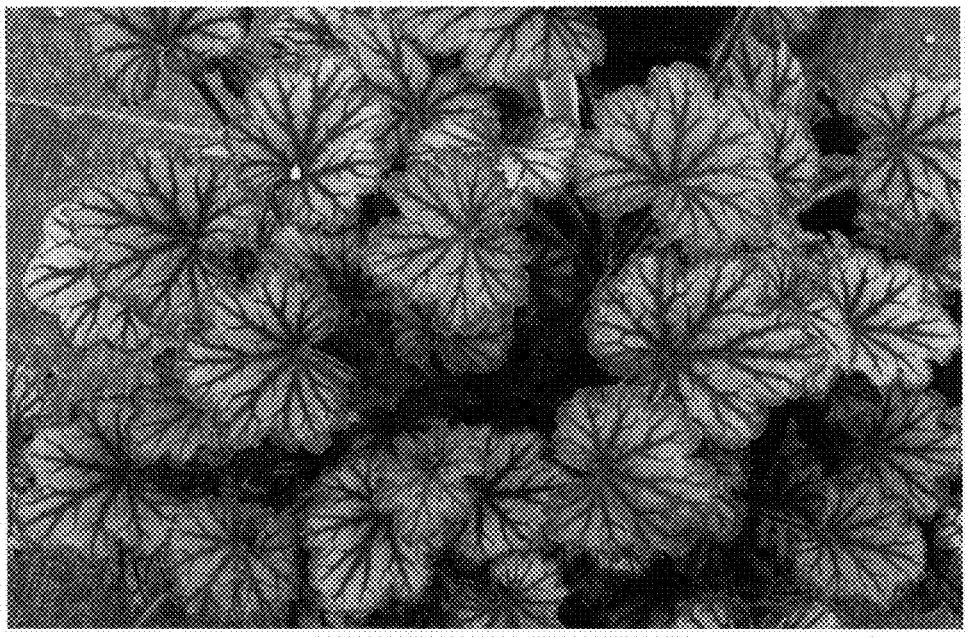
FIG. 1 above, FIG. 2 below